United States Patent
El Zabadani et al.

(10) Patent No.: US 7,339,493 B2
(45) Date of Patent: Mar. 4, 2008

(54) MULTIMEDIA CONTROLLER

(75) Inventors: Hicham Mahmoud El Zabadani, Beirut (LB); Abdelsalam A. Helal, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 500 days.

(21) Appl. No.: 10/889,155

(22) Filed: Jul. 12, 2004

(65) Prior Publication Data

US 2005/0062637 A1 Mar. 24, 2005

Related U.S. Application Data

(60) Provisional application No. 60/486,018, filed on Jul. 10, 2003, provisional application No. 60/490,717, filed on Jul. 29, 2003.

(51) Int. Cl.
*G08C 19/00* (2006.01)
*G05B 11/01* (2006.01)
*H04Q 7/20* (2006.01)
*H04L 17/02* (2006.01)

(52) U.S. Cl. .............................. 340/825.7; 340/825.72; 340/825.69; 340/825.52; 340/310.11; 455/434; 455/420; 455/419; 455/462; 341/176

(58) Field of Classification Search ........... 340/825.69, 340/825.72, 825.52, 310.11; 455/434, 420, 455/419, 462; 341/176
See application file for complete search history.

(56) References Cited

U.S. PATENT DOCUMENTS

| | | | |
|---|---|---|---|
| 5,671,267 A * | 9/1997 | August et al. ............... | 455/420 |
| 5,833,603 A | 11/1998 | Kovacs et al. | |
| 5,872,834 A | 2/1999 | Teitelbaum | |
| 6,204,763 B1 | 3/2001 | Sone | |
| 6,362,778 B2 | 3/2002 | Neher | |
| 6,380,858 B1 | 4/2002 | Yarin et al. | |
| 6,404,880 B1 | 6/2002 | Stevens | |
| 6,428,475 B1 | 8/2002 | Shen | |
| 6,453,027 B1 | 9/2002 | Kang et al. | |
| 6,496,111 B1 | 12/2002 | Hosack | |

(Continued)

OTHER PUBLICATIONS

Mann, W., et al., "Smart Phones for the Elders: Boosting the Intelligence of Smart Homes", Am. Assoc. for Artifical Intell. (AAAI), (Jul. 2002).

(Continued)

*Primary Examiner*—Jeffery Hofsass
*Assistant Examiner*—Scott Au
(74) *Attorney, Agent, or Firm*—Akerman Senterfitt (57) ABSTRACT

A portable communication device (200) can serve as a multimedia controller and can include a transceiver having wireless access to a client computer (510) coupled to a multimedia device (515, 520, and 525). The multimedia controller can also include a display (205) coupled to the transceiver (201), and a processor (202) coupled to the display and the transceiver. The processor can be programmed to send instructions to the client computer to perform at least one function among retrieving status information regarding the multimedia device, retrieving a program channel guide, controlling a recording function, selecting a program channel for display at the multimedia controller or selecting content from the client computer or a server coupled thereto for display at the multimedia controller. The processor can also be programmed to receive status information or content in response to sending instructions and to display the status information or content.

20 Claims, 4 Drawing Sheets

U.S. PATENT DOCUMENTS

| | | |
|---|---|---|
| 6,553,262 B1 | 4/2003 | Lang et al. |
| 6,567,672 B1 | 5/2003 | Park et al. |
| 6,678,516 B2 | 1/2004 | Nordman et al. |
| 6,774,795 B2 | 8/2004 | Eshelman et al. |
| 7,085,566 B1 * | 8/2006 | Burchard et al. ........... 455/434 |
| 2001/0046862 A1 | 11/2001 | Coppinger et al. |
| 2002/0060243 A1 | 5/2002 | Janiak et al. |
| 2002/0127145 A1 | 9/2002 | Der Ghazarian et al. |
| 2002/0128864 A1 | 9/2002 | Maus et al. |
| 2003/0009088 A1 | 1/2003 | Korth et al. |
| 2003/0013507 A1 | 1/2003 | Sato |
| 2003/0064732 A1 | 4/2003 | McDowell et al. |
| 2003/0064749 A1 | 4/2003 | Soini et al. |
| 2003/0083020 A1 | 5/2003 | Langford |
| 2003/0087628 A1 | 5/2003 | Michibata |

OTHER PUBLICATIONS

Haigh, K., et al., "The Role of Intelligent Technology in Elder Care", AAAI-02 WS on Automation as Caregiver, (Jul. 2002).

Giraldo, C., "mPCA-A Mobile Patient Care-Giving Assistant for Alzheimer Patients", UbiCog '02, (Sep. 29, 2002).

Helal, S., et al., "Smart Phone Based Cognitive Assistant", UbiHealth, (Oct. 12-15, 2003).

Helal, S., et al., "Assistive Environments for Successful Aging". UbiComp 2003, (2003).

Helal, S., et al., "Enabling Location-Aware Pervasive COmputing Applications for the Elderly", IEEE Conf. on Pervasive Computing & Comm. PerCom '03, (2003).

Helal, S., et al., "Assistive Environments for Elder Care—Integrating Smart Phones with Smart Homes", ICADI Conf. on Aging, (2003).

Long, M., "A New Reference Design for Jumpstarting Smartphone Development", E-inSITE, (Feb. 13, 2003).

"Home Automation Systems", National Security, Inc., Internet, viewed (Jun. 3, 2003).

"SmartPhones", Motorola, Internet, (viewed Jun. 3, 2003).

"An Executive White Paper—Secure Mobile Banking Architecture", Consumer Direct Link, Inc., (Sep. 2001).

Paron MPC, Consumer Direct Link, Inc., (2000-2001).

* cited by examiner

MULTIMEDIA CONTROLLER

CROSS-REFERENCE TO RELATED APPLICATIONS

This application claims the benefit of both U.S. Provisional Application No. 60/486,018, filed in the United States Patent and Trademark Office on Jul. 10, 2003, and U.S. Provisional Application No. 60/490,717 filed in the United States Patent and Trademark Office on Jul. 29, 2003, the entirety of both applications is incorporated herein by reference.

BACKGROUND OF THE INVENTION

1. Technical Field

This invention relates to the field of remote controllers and more particularly to a remote controller for multimedia applications.

2. Description of the Related Art

Remote controllers for multimedia devices are well known and two-way communication devices such as cellular phones are also commonplace. Remote controllers for television sets provide sufficient control of television sets but fail to provide adequate two-way communication functions such as cell phones. Cell phones provide adequate two-way communication functions, but are usually not ideal for remotely controlling a multimedia device. Furthermore, remote controllers tend not to be user friendly when attempting to control much more than a television set. Typically, television sets are now coupled to numerous devices such as VCRs, PVRs, cable set top boxes, satellite receiver boxes, and stereo systems for example. Controlling all the devices with the typical remote controller usually requires the devices to be in the presence of the television set to utilize the menu functions displayed thereon. It also typically requires multiple remote controllers. The melding of two-way communication device and a remote controller to send and retrieve meaningful information and to control the operation of such multimedia devices effectively have yet to be provided or disclosed.

SUMMARY OF THE INVENTION

In a first aspect of the invention, a multimedia controller includes a transceiver having wireless access to a client computer coupled to a multimedia device, a display coupled to the transceiver, and a processor coupled to the display and the transceiver. The processor can be programmed to send instructions to the client computer to perform at least one function among the functions of retrieving status information regarding the multimedia device, retrieving a program channel guide, controlling a recording function, selecting a program channel for display at the multimedia controller, and selecting content from the client computer or a server coupled thereto for display at the multimedia controller. The processor can also be programmed to receive status information or content in response to sending instructions and to display the status information or content.

In a second aspect of the invention, a multimedia controller system can include a multimedia device, a client computer coupled to the multimedia device, and a multimedia controller used to wirelessly send instructions to the client computer to control the multimedia device. The multimedia controller can include a transceiver having wireless access to the client computer, a display coupled to the transceiver, and a processor coupled to the display and the transceiver. Again, the processor can be programmed to send instructions to the client computer to perform at least one function among the functions of retrieving status information regarding the multimedia device, retrieving a program channel guide, controlling a recording function, selecting a program channel for display at the multimedia controller; and selecting content from the client computer or a server coupled thereto for display at the multimedia controller. The processor can also be programmed to receive status information or content in response to sending instructions and to display the status information or content.

In a third aspect of the invention, a method of remotely controlling a multimedia device including the steps of wirelessly transmitting instructions using a portable two-way communication device to a client computer coupled to the multimedia device to control the multimedia device, receiving status information or content in response to wirelessly transmitting instructions, and displaying the status information or content associated with the multimedia device at the portable two-way communication device.

BRIEF DESCRIPTION OF THE DRAWINGS

There are shown in the drawings embodiments which are presently preferred, it being understood, however, that the invention is not limited to the precise arrangements and instrumentalities shown.

DETAILED DESCRIPTION OF THE INVENTION

An embodiment in accordance with the present invention can include a system having a multimedia controller application which allows the user to be able to get TV channels listings, browse TV channels, record favorite TV shows, schedule recordings, watch prerecorded shows, listen to music, and finally view pictures. In one embodiment, such a system can include two parts, a first part written in J2ME or BREW for example can ideally run on a smart phone, and a second part written in Visual Basic 6 for example can run on a stand alone computer. The computer can be a regular computer on which a TV tuner card with Personal Video Recorder is plugged. It can also be a set-top box which is connected to the web through a Local Area Network or the cable company broadband service. The role of the application that runs on the computer can be to listen to any command that is getting from the phone through a network protocol such as UDP, and performs a certain operation accordingly. For example, suppose the user wants to watch TV, the user can run the application on the phone, browse through the menu, and choose "My TV". At that moment, the phone can send a UDP packet to the computer that says: "start TV", the computer will read the packet and turn the TV on.

The same concept applies for other features; however, some features require two-way interaction. For example, if user wants to get the TV listings for a specific channel he or she would choose the channel, open the menu, and choose TV listings. At that point, the phone may send to the computer a packet that says: "send me the listings for the specific channel", the computer can then execute this query and send the result back to the phone. The phone can then directly display the results on the phone's screen. Such a system can be implemented for example using an i95c Motorola smart phone, a Dell Computer having a Pentium-4 processor, and a plugged-in Hauppage winTV PVR-pci card.

Advantageously, such a system can be used both indoors and outdoors. In-door, the system helps the user control his/her media devices like a remote control. It has the power to control different kinds of media devices like TV, Music Player, Video Recorder and Picture Viewer. The system also can help a user listen to their music files, watch their TV channels, and enjoy the slide show of their pictures. Outdoor, the system helps the user get the programming guide information from the web, select a program, and schedule it to be recorded by the client computer when the scheduled time comes. It can also provide instant recording of the selected channel. Another impressing out-door functionality can enable the user to get his/her pictures into the smart phone.

Figure 1:
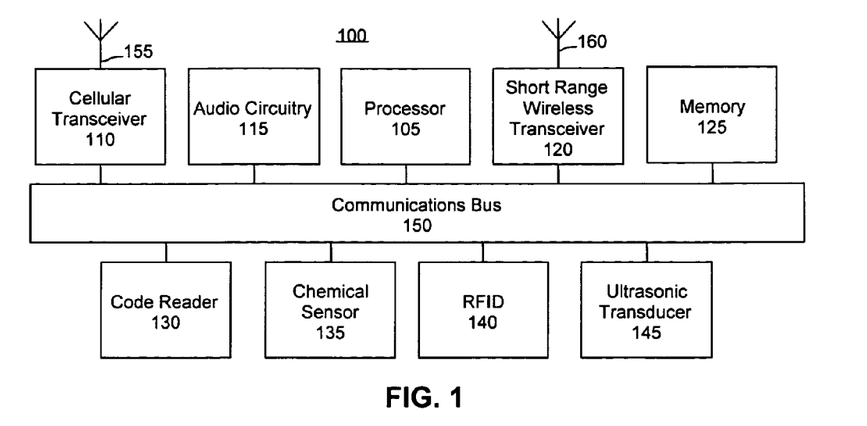
FIG. 1 is a schematic diagram illustrating an exemplary portable communications device (PCD) configured in accordance with the inventive arrangements.

FIG. 1 is a schematic diagram illustrating an exemplary portable communications device (PCD) 100 configured in accordance with the inventive arrangements disclosed herein. As shown, the PCD 100 can include a processor 105, a cellular transceiver 110, audio circuitry 115, a short range wireless transceiver 120, and a memory 125. Each of the aforementioned components can be communicatively linked via a suitable communications bus 150.

The processor 105 can execute a suitable operating system and one or more applications for controlling the various functions of the PCD 100. For example, the processor 105 can execute an operating system which can support the execution of one or more applications intended to run on that platform and which support operation of the various functions and features disclosed herein. For example, as the PCD 100 can include one or more sensors to be described in greater detail herein, the operating system and computing architecture can be designed to support the operation of such sensors.

The memory 125 can be implemented as random access memory (RAM), read-only memory (ROM), EPROM, or any other type of physical memory suitable for use within a portable computing device such as the PCD 100 or a portable or cellular telephone. It should be appreciated that the memory 125, while illustrated as a separate unit, can be incorporated into the processor 105 or another device. In any case, the memory 125 can include programmatic instructions to be executed by the processor 105 as well as any operational data necessary for operation of the PCD 100.

Wireless signals can be received and sent via the antenna 155 which can be suited for longer-range communications such as conventional cellular communications. Accordingly, the antenna 155 can be operatively connected to the cellular transceiver 110. Signals detected by antenna 155 can be provided to the cellular transceiver 110 for processing and decoding. For example, the cellular transceiver 110 can include a codec for coding and decoding information received or to be sent via wireless transmission. The transceiver 110 can make the decoded signals and/or information available to other components of the PCD 110 for processing. Outbound information received by the cellular transceiver 110 can be coded and/or formatted for wireless transmission by the codec and then provided to the antenna 155 for transmission.

Thus, it should be appreciated that the cellular communication device 100 can communicate via conventional cellular telephone calls and access wireless networks, for example using Wireless Access Protocol (WAP), IP or another suitable wireless communications protocol, such that the PCD 100 can access the Internet, the Web, a Local Area Network (LAN), and/or a wide area network (WAN), as well as any applications and/or services disposed on such networks via a wireless communications link.

The audio circuitry 115 can include a microphone or other transducive element (not shown) for receiving sound and one or more analog-to-digital converters (not shown) for digitizing the received sound. The audio circuitry 115 further can include one or more digital-to-analog converters (not shown) for converting digital information into sound. The audio circuitry 115 can include a speaker or other transducive element (not shown) for generating sound as well as one or more amplifiers (not shown). Notably, although not shown, the PCD 100 can include one or more audio output jacks and/or or other digital data interface ports.

It should be appreciated that the audio circuitry 115 can include additional processors, such as digital signal processors (DSP) as may be required for processing audio and performing functions such as audio encoding, audio decoding, noise reduction, and the like. For example, according to one embodiment of the present invention, the audio circuitry can be implemented using one or more discrete components. In another arrangement, the audio circuitry 115 can be implemented using one or more larger integrated circuits configured to perform the various functions disclosed herein. Thus, the PCD 100 can be configured to play various audio formats from streaming formats to MP3's, or other audio file formats such as .wav or .aiff files.

The PCD 100 also can include a short range wireless transceiver 120 as well as an antenna 160 operatively connected thereto. The short range wireless transceiver 120 can both send and receive data. For example, according to one embodiment of the present invention, the short range wireless transceiver 120 can be implemented as a Bluetooth-enabled wireless transceiver, or as a transceiver configured to communicate with one of the 802.11 family of short range wireless communications specifications. The short range wireless transceiver 120 and accompanying antenna 160 can be configured to communicate using any of a variety of short range, wireless communications protocols and/or systems. Accordingly, the various examples disclosed herein have been provided for illustration only and should not be construed as a limitation of the present invention. For example, another short range wireless communication protocol could also include infrared communications.

The PCD 100 can include a plurality of sensor devices such as a code reader 130, a chemical sensor 135, a radio frequency identification (RFID) mechanism 140, and an ultrasonic transducer 145. The code reader 130 can be an optical device capable of reading various coding schemes such as bar codes, or other visual patterns, including, but not limited to, single and/or multi-dimensional bar codes or other visual coding schemes. The code reader 130 can include a scanning device capable of directing a beam of light across the visual code and measuring the amount of light that is reflected back as dark areas reflect less light than white or lighter areas. The scanner converts the light energy into electrical energy, which is then converted to data by a codec.

The ultrasonic transponder 145 can include a transceiver capable of transmitting a beacon signal which can be received by one or more ultrasonic transceivers. The use of an ultrasonic transponder 145 enables high precision tracking technology to be used within one's house, for example, in the case where one's home is outfitted with one or more ultrasonic transceivers. Accordingly, a home or other "smart" environment, for example one equipped with a ultrasonic transceiver, can detect when a user having the PCD 100 is within a particular range of the transceiver. Thus, determinations can be made as to whether a person is located within the home or environment. If within a home, a determination can be further made as to which room the person is in at a given time. This enables the PCD 100 device to control the multimedia outlet anywhere in the house.

The PCD 100 also can include a variety of other sensors which have not been illustrated in FIG. 1. For example, the PCD 100 can include a temperature sensor capable of sensing the temperature of a user when held. Similarly, the temperature sensor, or another such temperature sensor, can be configured to measure the ambient temperature of a room or other environment. A global positioning system module also can be included within the PCD 100. Also, an infrared transceiver can be incorporated into the device for communication with other devices so configured. According to one embodiment of the present invention, a conventional telephone jack or port can be included in the PCD 100 such that a user need only plug the PCD 100 into a standard wall jack to initiate telephone calls over the Public Switched Telephone Network (PSTN). Such an arrangement can be advantageous in situations where wireless cellular connectivity may not be available or is intermittent.

The PCD 100 also can include one or more biological sensors. For example, a sensor for measuring heart rate and a galvanic skin sensor can be included for detecting anxiety related conditions within a user. Still, other sensors can be included such as fingerprint detection sensors and the like. The listing of biological sensors is not intended as a limitation of the present invention, but rather as examples intended to broaden the scope of the inventive arrangements disclosed herein.

Each of the various components of the PCD 100 disclosed herein can be communicatively linked with one another using appropriate circuitry, whether through the memory 125, one or more additional memories (not shown), the processor 105, one or more additional interface processors or logic controllers (not shown), and/or the communications bus 150. For example, while each of the sensors described herein is depicted as being linked to the communications bus 150, it should be appreciated that each sensor can be configured to communicate with the processor 105 through a suitable interface, such as a digital input and/or output or through an intermediate interface processor, for example using an interrupt request of the processor.

Additionally, one skilled in the art will recognize that the various components disclosed herein can be embodied in various other forms and that the configuration disclosed and described with reference to FIG. 1 is provided for purposes of illustration only. For example, the various components can be implemented as one or more discrete components, as one or more processors, logic controllers, and/or DSP's, or any combination thereof.

Figure 2:
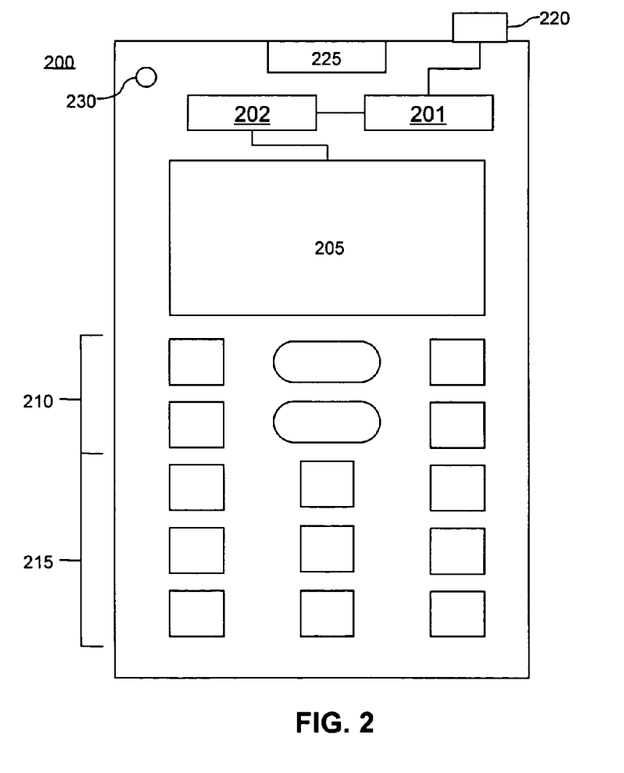
FIG. 2 is schematic diagram illustrating an exemplary cellular communication device in accordance with the inventive arrangements.

FIG. 2 is a schematic diagram illustrating an exemplary cellular communication device 200 in accordance with the inventive arrangements disclosed herein. As shown, the cellular communication device (PCD) 200 can include a transceiver 201 coupled to a processor 202 and a display screen 205, one or more control or operational keys 210, which can include special function command keys for operation of one or more of the functions disclosed herein, alphanumeric keys or buttons 215, and an antenna 220 (which may be configured to be fully located within the PCD 200). The PCD 200 further can include a battery or other power source (not shown).

The physical arrangement of the PCD 200 has been provided for purposes of illustration only. As such, it should be appreciated that the various components can be located in any of a variety of different configurations. For example, the PCD 200 can include additional keys or controls disposed on frontal portion or the sides of the unit.

According to one embodiment of the present invention, the physical arrangement of the PCD 200 can be conducive for use by older persons or those that may have difficulty accessing and/or operating the various keys and/or controls of conventional cellular telephones, such as persons with physical disabilities or other infirmities. For example, the control keys 210 and the alphanumeric keys 215 of the PCD 200 can be larger in size than conventional cellular device keys and can be spaced a greater distance from one another with respect to both the width and length of the PCD 200. That is, the horizontal key spacing and the vertical key spacing can be greater than that found with conventional cellular devices.

Similarly, the display screen 205 can be larger than those found on conventional cellular devices and have an increased contrast ratio if so desired. The display screen 205 can be a liquid crystal display (LCD) implemented in either grayscale or color, or any other type of suitable display screen. It should be appreciated that any of a variety of different display screens, including touchscreens, can be used within the PCD 200. Selection of a particular display screen 205 should not be construed as a limitation of the present invention.

The battery can be designed to operate for extended times. Additionally, while the various enhancements disclosed herein may add size to the PCD 200, it is expected that the increased size would be an acceptable tradeoff for increased functionality and ease of use provided by the PCD 200.

As noted, the PCD 200 can include a variety of sensors. As shown in FIG. 2, the PCD 200 can be configured with a code reader 225. While the code reader 225 can be positioned on the PCD 200 in any of a variety of different locations, according to one embodiment, the code reader can be positioned at the top portion of the PCD 200. Other sensors can be located throughout the exterior portion of the PCD 200. For example, a temperature sensor 230 for measuring ambient temperature of an environment can be located near the top or bottom of the PCD 200 such that when held, the sensor is not obstructed by the hand of a user. In contrast, a sensor for measuring heart rate, skin resistivity, and/or body temperature can be positioned to come in contact with a hand of a user when the PCD 200 is held. For example, such sensors can be disposed on the backside or on either side portion of the PCD 200.

Figure 3:
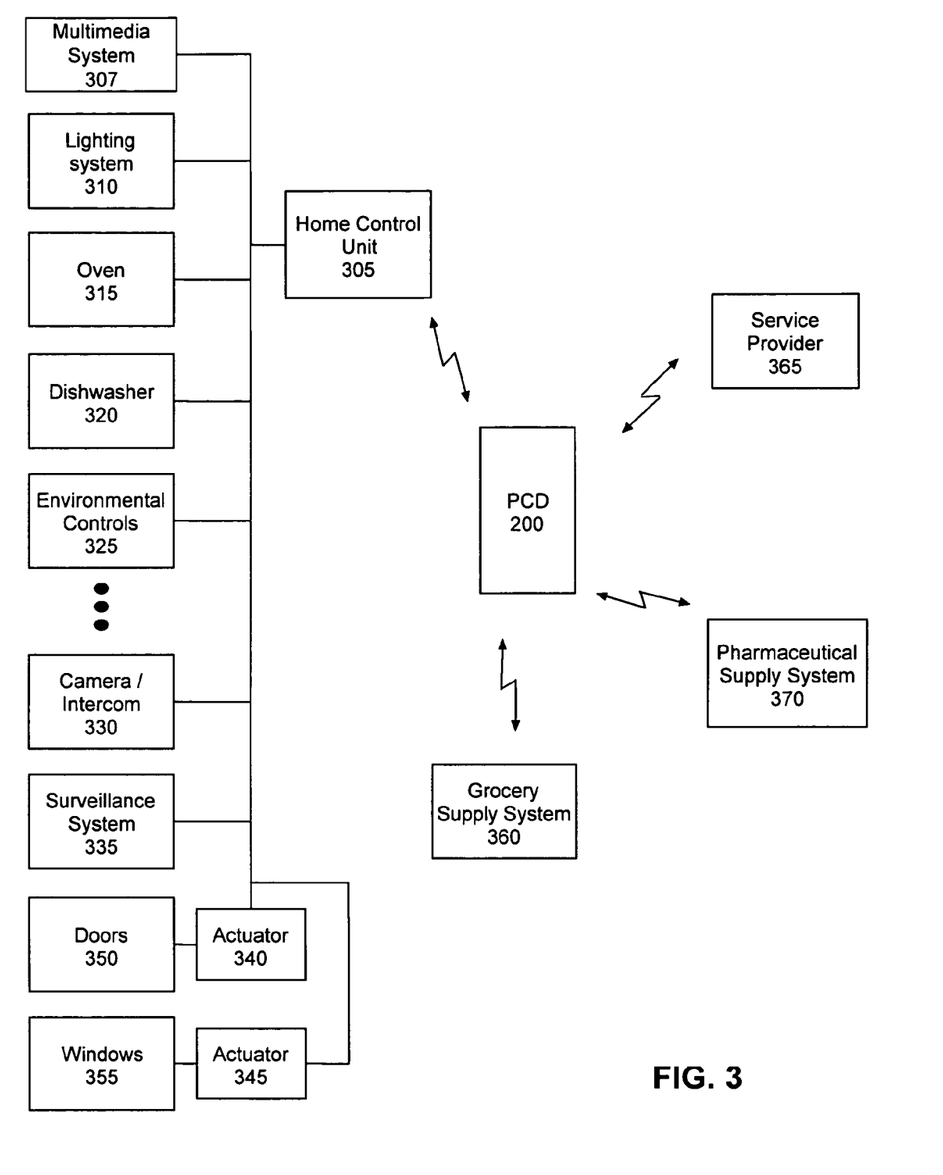
FIG. 3 is a schematic diagram illustrating various uses and applications of the PCD in accordance with the present invention.

FIG. 3 is a schematic diagram illustrating various uses and applications of the PCD 200 as disclosed herein. The PCD 200 can be designed to meet a variety of needs of elder persons. According to one aspect of the present invention, the PCD 200 can interact with a smart space, that is an environment equipped with suitable transceivers, communications equipment, and other controller units. For example, a home can be so configured. A home, workspace, caretaking facility, and/or other space that can be occupied and/or inhabited by persons can be configured with a central computing system designed to control one or more aspects of that environment including, but not limited to appliances, lighting, climate control, intercom systems, cameras, audio equipment, surveillance systems, and the like.

Thus, as shown in FIG. 3, the PCD 200 in one embodiment can communicate with a home control unit 305. Through the home control unit 305, the user of PCD 200 can access any of a variety of different systems and/or appliances including a multimedia system 307. The PCD 200 can access one or more lights, including one or more lighting systems 310, oven 315, dishwasher 320, environmental controls 325, for example heating and cooling controls and/or thermostats, as well as other appliances having the ability to communicate and respond to remote operational controls, such as washers, dryers, dishwashers, stoves, and the like. Additional systems such as cameras and/or intercoms 330, including other visual and/or audio-based systems, including surveillance systems 335, any of which can be wired for use inside and/or outside of a home can be communicatively linked to the home control unit 305 and can be controlled via the PCD 200.

The PCD 200 can include one or more application programs which allow the user to access the functionality of the various systems and/or devices connected to the home control unit 305. Accordingly, the user can check the status of any devices so connected to the home control unit 305 to determine whether the device is on, off, turn the device on or off, set the device to automatically start or stop at predetermined times, and change settings of the device, for example change a thermostat setting with respect to heating and/or cooling, or turn on heated dry cycle in the dishwasher. Similarly, applications can be configured enabling the PCD 200 to control lighting. Accordingly, using an appropriate application, the PCD 200 can turn lights on or off, dim lights, and set timing features so that lights turn on or off automatically at predetermined times, etc.

The PCD 200 can communicate with the home control unit 305 using any of a variety of different communications mechanisms. For example, the PCD 200 can initiate cellular telephone and/or conventional telephone calls to the home control unit 305 when the PCD 200 is not located within or proximate to the home within which the home control unit 305 is disposed. The PCD 200 can communicate with the home control unit using short range wireless communications when in range.

With respect to audio, video (visual), and audiovisual systems, the PCD 200 can access an audio feed, a video feed, and/or an audiovisual feed, as well as receive audio and/or video files. For example, the PCD 200 can receive a media stream via short range wireless communications, long range wireless communications, and/or wired communications as previously discussed. Accordingly, through the PCD 200 a user can view visitors at the front door if a camera is suitably positioned and communicatively linked with the home control unit 305. The PCD 200 further can receive audio from audio and/or surveillance systems or from a multimedia system. Notably, if a stereo is capable of linking with the home control unit 305, then the PCD 200 can be used to control the stereo as well as receive audio from the stereo such that one could listen to the stereo via the PCD 200.

Also, as shown, the home control unit 305 can be communicatively linked with one or more actuators 340 and 345 for controlling doors 350 and windows 355 respectively. Each controllable window 355 and/or door 350 can be equipped with an actuator capable of locking, unlocking, opening, and/or closing the window or door. Each actuator 340 and 345 can be activated responsive to control signals received from the home control unit 305. Thus, doors 350 and windows 355 can be remotely controlled so that the doors 350 and windows 355 can be automatically locked, unlocked, opened or closed varying amounts.

It should be appreciated that while smart spaces have been described with reference to a single, centralized computer system, one or more computer systems can be included. For example, lighting can be controlled with one computer system while temperature is controlled by another, and appliances can be controlled by yet another computer system. The various computer systems may or may not communicate with one another so long as each is able to communicate with the PCD 200. Still, each system can be configured to communicate with the PCD 200 independently and operate on its own. For instance, each appliance can be a "smart" appliance having built-in communications and control mechanisms for being accessed remotely. In that case, each appliance need not communicate with other appliances or a centralized computing system so long as the appliance and/or system can communicate directly with the PCD 200.

As shown with reference to the above discussion, the PCD 200 can provide a user with an integrated means for controlling many, if not most or all, aspects of one's home. User's can be provided with intuitive interfaces as well as audio notifications for the various functions disclosed herein. The present invention further can provide users with a level of comfort knowing that various appliances and systems of one's home can be checked when away from home, or simply when retiring for the evening without leaving the comfort of one's room.

Another aspect of the present invention can include using the PCD 200 to order groceries from a grocery supply system 360. The PCD 200 can be loaded with an application configured to aid a user in ordering groceries. For example, in the case where a market has provided a grocery order system, such the grocery supply system 360, that can be accessed via telephone, the Web, or another network connection, the user of the PCD 200 can place grocery orders.

Notably, as potential users of the PCD 200 may have particular dietary needs, the PCD 200 can be programmed to include any dietary restrictions and/or particular foods that the user requires. For example, the PCD 200 can be programmed with one or more rules specifying which items may or may not be purchased by the user. The PCD 200 can be configured to warn a user that the item being ordered is not an approved item or the PCD 200 simply can prevent the user from ordering such an item. Alternatively, the PCD 200 can be programmed with nutritional data concerning particular foods such that as a user orders items, a running nutritional count with respect to the foods that the user is ordering can be tracked, for example in terms of caloric intake, fat, cholesterol, saturated fat, and the like.

Information such as dietary requirements can be downloaded from a trusted source, such as a doctor's Web site, from a user computer, can be read from a visual code using the code reader, or via any other means, including, but not limited to using a charging cradle with the ability to synchronize with a computing source, whether local or not.

According to another embodiment of the present invention, the PCD 200 can be configured to call one or more service providers 365. For example, the PCD 200 can be programmed to call medical service providers such as doctors, nurses, emergency personnel, and other third party services. The PCD 200 can be programmed to contact such service providers 365 upon request of the user and/or automatically upon the occurrence of a detected event. For example, if a biosensor of the PCD 200 detects abnormal physiological data from the user, the PCD 200 can automatically contact a doctor, nurse, 911, and/or a family member or friend. That is the PCD 200 can include profile information or access profile information that can be stored on a local user computer system or on a computer system of a medical service provider. Accordingly, the health related or biological data detected by the PCD 200 regarding the user is obtained, such information can be compared with known baselines for that user.

According to another embodiment of the present invention, the PCD 200 can be programmed to communicate with a pharmaceutical supply system 370. For example, the PCD 200 can be programmed with a listing of each medication and/or prescribed substance a user is to take as well as the dosage guidelines and/or any other instructions including side effects pertaining to the medications. Accordingly, the PCD 200 can be used to automatically order refills, for example after a predetermined amount of time has passed. As the PCD 200 can be programmed with user prescription data including the time when medications are to be taken and dosages, the PCD 200 can calculate when the prescription is to be refilled.

Thus, the PCD 200 can remind the user, for example via an audio notification or a visual notification, to take particular medications at particular times and can remind a user to order or obtain a refill. Notably, the PCD 200 can require the user to respond to such a reminder or notification such that if no response is received, the PCD 200 can implement a programmatic action. For example, the PCD 200 can be programmed to contact a family member or a medical service provider. Such persons can be contacted via a page, an electronic mail, a text message, and/or a programmed audio message, for example after initiating a landline and/or cellular telephone call.

In another embodiment, the PCD 200 can be configured to automatically order a refill for the user by contacting the pharmaceutical supply 370. The pharmaceutical supply can be implemented as a Web site, an automated phone service, or another network accessible system. For example, the PCD 200 can place an order through a Web site, be programmed to leave an automated message on a pharmacy voice mail for reordering additional medication, or contact the pharmaceutical supply system 370 by establishing a communications link via another network connection.

The inventive arrangements disclosed herein can be used within a variety of additional applications. For example, according to one embodiment of the present invention, the PCD 200 can include a medical assistant application. The medical assistant application can remind an elder user, or any user for that matter, of the times when the user is to take medication. The PCD 200 can be used to scan the barcode printed on a prescription label. The PCD 200 then can retrieve information regarding the medicine from the pharmacy. For example, the PCD 200 can retrieve the times when the user is to take a prescribed medication as well as the dosage to be taken. The PCD 200 can provide the user with alarms and intelligent reminders to take medication. The PCD 200 further can obtain and provide information about medicines, allergies, and side effects. The PCD 200 can track the quantity of the medicine and automatically order the medicine if quantity falls below a certain predetermined threshold. The medical assistant application further can be used to arrange home delivery.

Figure 4:
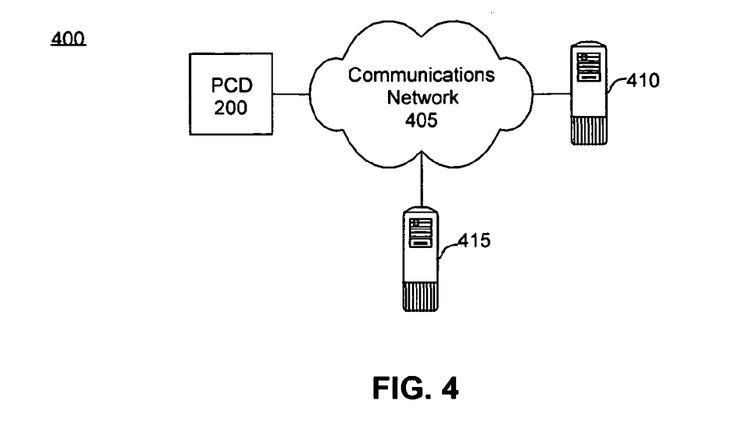
FIG. 4 is a schematic diagram of a remote controller system in accordance with an embodiment of the present invention.

FIG. 4 is a schematic diagram illustrating an exemplary system 400 supporting such an implementation. The system 400 can include a medical assistant application executing within the PCD 200, a proxy server 415, and a pharmacy server 420, each communicatively linked via a communications network 405. Notably, the PCD 200 can be communicatively linked to the communications network 405 via any suitable connection, whether wireless or wired. The client, or PCD 200, can initiate a communications link with the pharmacy server 410 via the proxy server 415. The PCD 200 then can scan the prescription label or other bar code disposed on medication, obtain information about the medication from the pharmacy, as well as receive a list of current medicines that the user is taking.

The proxy server 415 can listen for requests from the client PCD 200. Once a request, such as a Universal Datagram Packet (UDP), is received, the proxy server 415 can extract the RX number and pharmacy server 410 address. Accordingly, the proxy server 415 can provide the RX number to the pharmacy server 410 via a Hypertext Transfer Protocol (HTTP) request. The user, or operator of the PCD 200, can be authenticated by the pharmacy server 410. Upon successful authentication of the user, the pharmacy server 410 can provide requested information within an electronic document such as a Hypertext Markup Language (HTML) document, an Extensible Markup Language (XML) document, or the like. The proxy server 415 can parse the received information and send the information to the PCD 200 in a format used by the PCD 200 client. If the authentication is unsuccessful, the pharmacy server 410 can send a failure message to the PCD 200.

Figure 5:
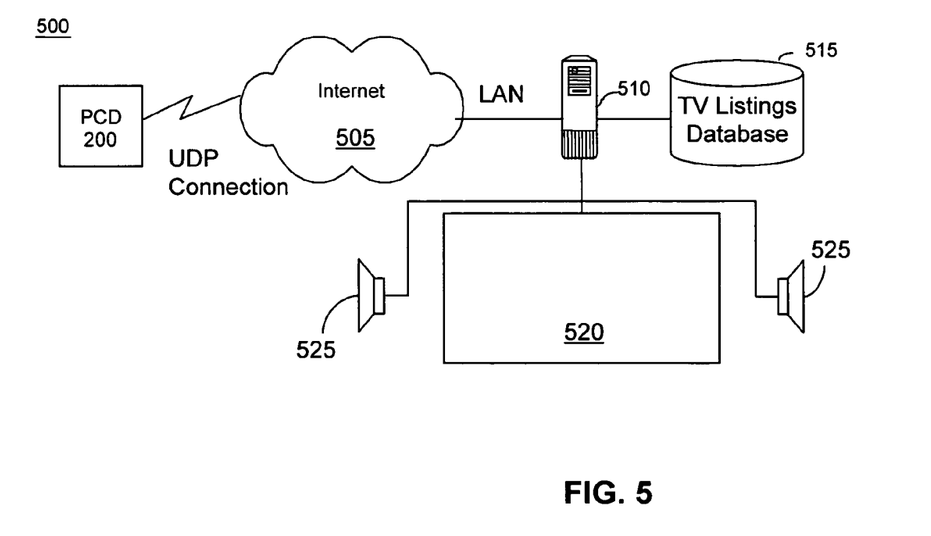
FIG. 5 is a schematic diagram of another remote controller system in accordance with an embodiment of the present invention.

Referring to FIG. 5, a multimedia controller such as the PCD 200 can include a transceiver having wireless access to a client computer 510 coupled to a multimedia device (515, 520, and 525), a display coupled to the transceiver, and a processor coupled to the display and the transceiver. The processor can be programmed to send instructions to the client computer 510 to perform at least one function among the functions of retrieving status information regarding the multimedia device, retrieving a program channel guide, controlling a recording function, selecting a program channel for display at the multimedia controller; and selecting content from the client computer or a server coupled thereto for display at the multimedia controller. The processor can also be programmed to receive status information or content in response to sending instructions and to display the status information or content. The transceiver can be part of a cellular phone or smart phone and the multimedia device can be for example a television set, a video recorder, an MP3 player, a music player, or a picture viewing device. The status information or content received by the multimedia controller can be television channel listings, music station channel listings, thumbnail sketches of channel listings, recording schedules, or status settings. As previously mentioned, the wireless access connection to the client computer 510 can be a Universal Datagram Packet connection from the multimedia controller 200 to the client computer via a network connection such as the internet 505 or possibly a direct connection via an infrared connection from the multimedia controller to the client computer 510. Note that the wireless access to the client can include at least one transceiver that communicates with the client computer directly in a shorter range and alternatively communicates with the client computer via a wireless network.

Figure 6:
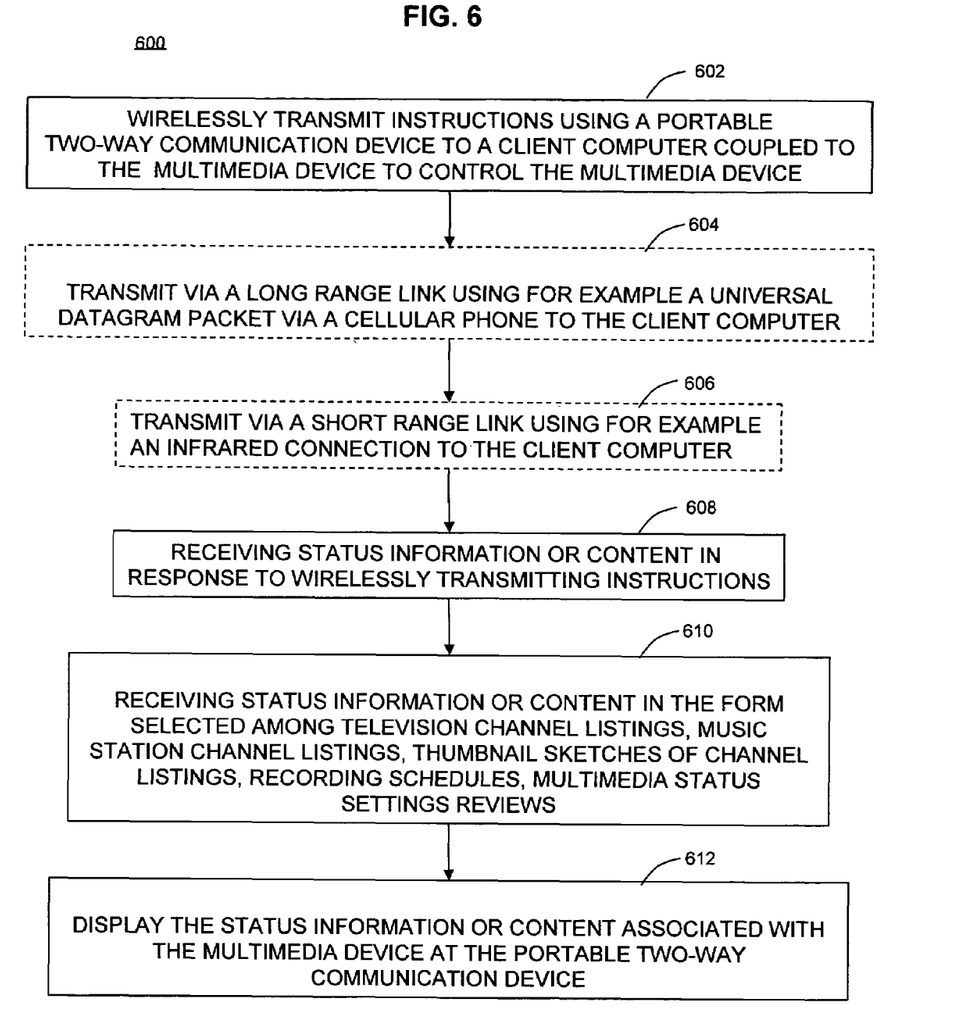
FIG. 6 is a flow chart illustrating a method of remotely controlling a multimedia device in accordance with an embodiment of the present invention.

Referring to FIG. 6, a flow chart illustrating method 600 of remotely controlling a multimedia device includes the step 602 of wirelessly transmitting instructions using a portable two-way communication device to a client computer coupled to the multimedia device to control the multimedia device, receiving status information or content in response to wirelessly transmitting instructions at step 608, and displaying the status information or content associated with the multimedia device at the portable two-way communication device at step 612. The step of transmitting instructions can include the optional step 604 of transmitting via a long range link using for example a Universal Datagram Packet via a cellular phone to the client computer or alternatively the step 606 of transmitting via a short range link for example using an infrared connection to the client computer. The step of receiving can include the step of receiving status information or content at step 610 in the form selected among television channel listings, music station channel listings, thumbnail sketches of channel listings, recording schedules, or multimedia status settings. Note that the steps of transmitting and receiving can include communicating directly with the client computer in a short range and alternatively communicating with the client computer using a wireless network coupled to the internet.

While the inventive arrangements disclosed herein have been described with reference to use by elder persons, it should be appreciated that such configurations also can be useful for other persons having physical or cognitive limitations and/or disabilities. Accordingly, the present invention should not be construed to be used solely for elder persons, or disabled persons for that matter.

Additionally, it should be appreciated that the present invention can include a user profile including timing information specifying particular times when the user is to be located at home, when lights are to be turned off, when medications are to be taken, and time guidelines for other aspects of one's life. In any situation where the PCD 200 is to remind the user through a notification, the PCD 200 can be programmed to await a response. If no response is received, the PCD 200 can be configured to notify one or more persons and/or computing systems as described herein.

The present invention can be realized in hardware, software, or a combination of hardware and software. The present invention can be realized in a centralized fashion in one computer system, or in a distributed fashion where different elements are spread across several interconnected computer systems. Any kind of computer system or other apparatus adapted for carrying out the methods described herein is suited. A typical combination of hardware and software can be a general purpose computer system with a computer program that, when being loaded and executed, controls the computer system such that it carries out the methods described herein.

Notably, the PCD 200 can be configured to notify one or more persons, whether family, friends, or medical personnel in the event that the user does not follow one or more of the guidelines programmed into the PCD 200. Such guidelines can include, but are not limited to, deviating from a particular dietary plan, not being located at home during certain time periods, not responding to reminders to take medications, and the like. Persons can be notified using any of a variety of different messaging techniques. For example, the PCD 200 can be configured to send predetermined audio messages, text messages, electronic mail messages, pages, telephone calls, including calls to 911, and the like.

The present invention also can be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

This invention can be embodied in other forms without departing from the spirit or essential attributes thereof. Accordingly, reference should be made to the following claims, rather than to the foregoing specification, as indicating the scope of the invention.

What is claimed is:

1. A multimedia controller, comprising:
a transceiver having wireless access to a client computer coupled to a number of multimedia devices;
a display coupled to the transceiver;
audio circuitry coupled to the transceiver;
a processor coupled to the display, audio circuitry, and the transceiver, wherein the processor receives and stores program instructions for:
sending instructions to the client computer to perform the functions of retrieving status information regarding the multimedia device, retrieving a program channel guide, controlling a recording function, selecting a program channel for display at the multimedia controller, and selecting content from the client computer or a server coupled thereto
receiving status information or content in response to sending instructions;
displaying the status information or content; and
rendering selected content received from the client computer or server, the content comprising visual content that is rendered on the display or audio content that is rendered through the audio circuitry;
a bus communicatively linked to transceiver, display, audio circuitry, and processor; and
a plurality of sensors communicatively linked through the bus to the processor, wherein the sensors include a transponder for tracking movements of a user within a smart environment and at least one of a code reader having an optical scanning device for reading bar codes, a combination heart-rate sensor and galvanic skin sensor for detecting an anxiety-related condition of the user, and a radio frequency identification (RFID) sensor.

2. The multimedia controller of claim 1, wherein the transceiver is part of a cellular phone or a smart phone, with or without wireless LAN capability.

3. The multimedia controller of claim 1, wherein the multimedia device is selected from the group comprising a television set, LCD panel display, a video recorder, an MP3 player, a music player, and a picture viewer.

4. The multimedia controller of claim 1, wherein the status information or content received by multimedia controller is selected among television channel listings, music station channel listings, thumbnail sketches of channel listings, recording schedules, review multimedia status settings.

5. The multimedia controller of claim 1, wherein the wireless access to the client computer comprises a infrared connection from the multimedia controller to the client computer.

6. The multimedia controller of claim 1, wherein the wireless access to the client computer comprises a Universal Datagram Packet connection from the multimedia controller to the client computer.

7. The multimedia controller of claim 1, wherein the wireless access to the client comprises at least one transceiver that communicates with the client computer directly in a shorter range and alternatively communicates with the client computer via a wireless network.

8. A multimedia controller system, comprising:
a multimedia device;
a client computer coupled to the multimedia device; and
a multimedia controller used to wirelessly send instructions to the client computer to control the multimedia device, wherein the multimedia controller comprises:
  a transceiver having wireless access to the client computer;
  a display coupled to the transceiver;
  audio circuitry coupled to the transceiver;
  a processor coupled to the display, audio circuitry, and the transceiver, wherein the processor receives and stores program instructions for:
    sending instructions to the client computer to perform he functions of retrieving status information regarding the multimedia device, retrieving a program channel guide, controlling a recording function, selecting a program channel for display at the multimedia controller, and selecting content from the client computer or a server coupled thereto;
    receiving status information or content in response to sending instructions;
    displaying the status information or content; and
    rendering selected content received from the client computer or server, the content comprising visual content that is rendered on the display or audio content that is rendered through the audio circuitry;
  a bus communicatively linked to transceiver, display, audio circuitry, and processor; and
  a plurality of sensors communicatively linked through the bus to the processor, wherein the sensors include a transponder for tracking movements of a user within a smart environment and at least one of a code reader having an optical scanning device for reading bar codes, a combination heart-rate sensor and galvanic skin sensor for detecting an anxiety-related condition of the user a radio frequency identification (REID) sensor.

9. The multimedia controller system of claim 8, wherein the transceiver is part of a cellular phone or a smart phone.

10. The multimedia controller system of claim 8, wherein the multimedia device is selected from the group comprising a television set, an LCD Panel display, a video recorder, an MP3 player, a music player, and a picture viewer.

11. The multimedia controller system of claim 8, wherein the status information or content received by multimedia controller is selected among television channel listings, music station channel listings, thumbnail sketches of channel listings, recording schedules, review multimedia status settings.

12. The multimedia controller system of claim 8, wherein the wireless access to the client computer comprises a infrared connection from the multimedia controller to the client computer.

13. The multimedia controller system of claim 8, wherein the wireless access to the client computer comprises a Universal Datagram Packet connection from the multimedia controller to the client computer via a network.

14. The multimedia controller system of claim 8, wherein the wireless access to the client comprises at least one transceiver that communicates with the client computer directly in a shorter range and alternatively communicates with the client computer via a wireless network.

15. A method of remotely controlling a multimedia device, comprising the steps of:
  programming instructions executable by a processor contained in a portable two-way communication device;
  wirelessly transmitting the instructions using the portable two-way communication device to a client computer coupled to the multimedia device to control the multimedia device;
  receiving by the portable two-way communication device status information or content in response to wirelessly transmitting instructions;
  rendering the status information or content associated with the multimedia device at the portable two-way communication device; and
  performing a plurality of sensing functions using a plurality of sensors communicatively linked to the processor, the sensors including a transponder for tracking movements of a user within a smart environment and at least one of a code reader having an optical scanning device for reading bar codes, a combination heart-rate sensor and galvanic skin sensor for detecting an anxiety-related condition of the user, and a radio frequency identification (RFID) sensor.

16. The method of claim 15, wherein the step of transmitting instructions comprises transmitting a Universal Datagram Packet via a cellular phone to the client computer.

17. The method of claim 15, wherein the multimedia device is selected from the group comprising a television set, a video recorder, an MP3 player, a music player, and a picture viewer.

18. The method of claim 15, wherein the step of receiving comprises the step of receiving status information or content in the form selected among television channel listings, music station channel listings, thumbnail sketches of channel listings, recording schedules, multimedia status settings reviews.

19. The method of claim 15, wherein the step of wirelessly transmitting comprises transmitting via an infrared connection to the client computer.

20. The method of claim 15, wherein the steps of wirelessly transmitting and receiving comprises communicating directly with the client computer in a short range and alternatively communicating with the client computer using a wireless network coupled to the internet.

* * * * *